United States Patent
Lee et al.

(10) Patent No.: US 10,408,780 B2
(45) Date of Patent: Sep. 10, 2019

(54) STRUCTURE OF GAS SENSOR

(71) Applicant: UNITED MICROELECTRONICS CORPORATION, Hsinchu (TW)

(72) Inventors: Chia-Wei Lee, Kaohsiung (TW); Chang-Sheng Hsu, Hsinchu (TW); Chih-Fan Hu, Taoyuan (TW); Chin-Jen Cheng, Zhubei (TW); Chang Hsin Wu, Zhudong Township (TW)

(73) Assignee: UNITED MICROELECTRONICS CORPORATION, Hsinchu (TW)

( * ) Notice: Subject to any disclaimer, the term of this patent is extended or adjusted under 35 U.S.C. 154(b) by 50 days.

(21) Appl. No.: 15/493,120

(22) Filed: Apr. 20, 2017

(65) Prior Publication Data

US 2018/0306738 A1 Oct. 25, 2018

(51) Int. Cl.
*G01N 27/12* (2006.01)

(52) U.S. Cl.
CPC .................. *G01N 27/128* (2013.01)

(58) Field of Classification Search
CPC .................. G01N 27/123; G01N 27/128
See application file for complete search history.

(56) References Cited

U.S. PATENT DOCUMENTS

| | | | |
|---|---|---|---|
| 4,668,374 A * | 5/1987 | Bhagat | G01N 27/4071 204/412 |
| 7,487,675 B2 * | 2/2009 | Ikawa | G01F 1/6845 73/204.26 |
| 7,655,333 B2 | 2/2010 | Huang et al. | |
| 8,961,760 B2 | 2/2015 | Fix et al. | |
| 2002/0142478 A1 | 10/2002 | Wado et al. | |
| 2005/0205959 A1 * | 9/2005 | Chau | B81B 7/0041 257/467 |
| 2007/0062812 A1 * | 3/2007 | Weber | G01N 27/128 204/431 |
| 2008/0134753 A1 * | 6/2008 | Jun | G01N 27/128 73/23.2 |
| 2015/0153294 A1 * | 6/2015 | Watanabe | G01N 27/16 73/25.03 |
| 2015/0226688 A1 * | 8/2015 | Watanabe | G01N 27/18 73/31.05 |
| 2016/0084786 A1 * | 3/2016 | Suzuki | G01N 27/16 73/31.06 |
| 2017/0212070 A1 * | 7/2017 | Lee | H01L 29/66007 |

* cited by examiner

*Primary Examiner* — Marrit Eyassu
(74) *Attorney, Agent, or Firm* — Ding Yu Tan

(57) ABSTRACT

The present invention provides a structure of a gas sensor, comprising: a support, having a front side, a back side opposite to the front side, a cell region, and a peripheral region circling the cell region; a cavity, formed on the back side of the support in the cell region; a heater, disposed on the front side of the support covering the cavity; a sensing element, disposed on the heater; and a sealing layer, formed on the back side of the support covering inside the cavity.

10 Claims, 1 Drawing Sheet

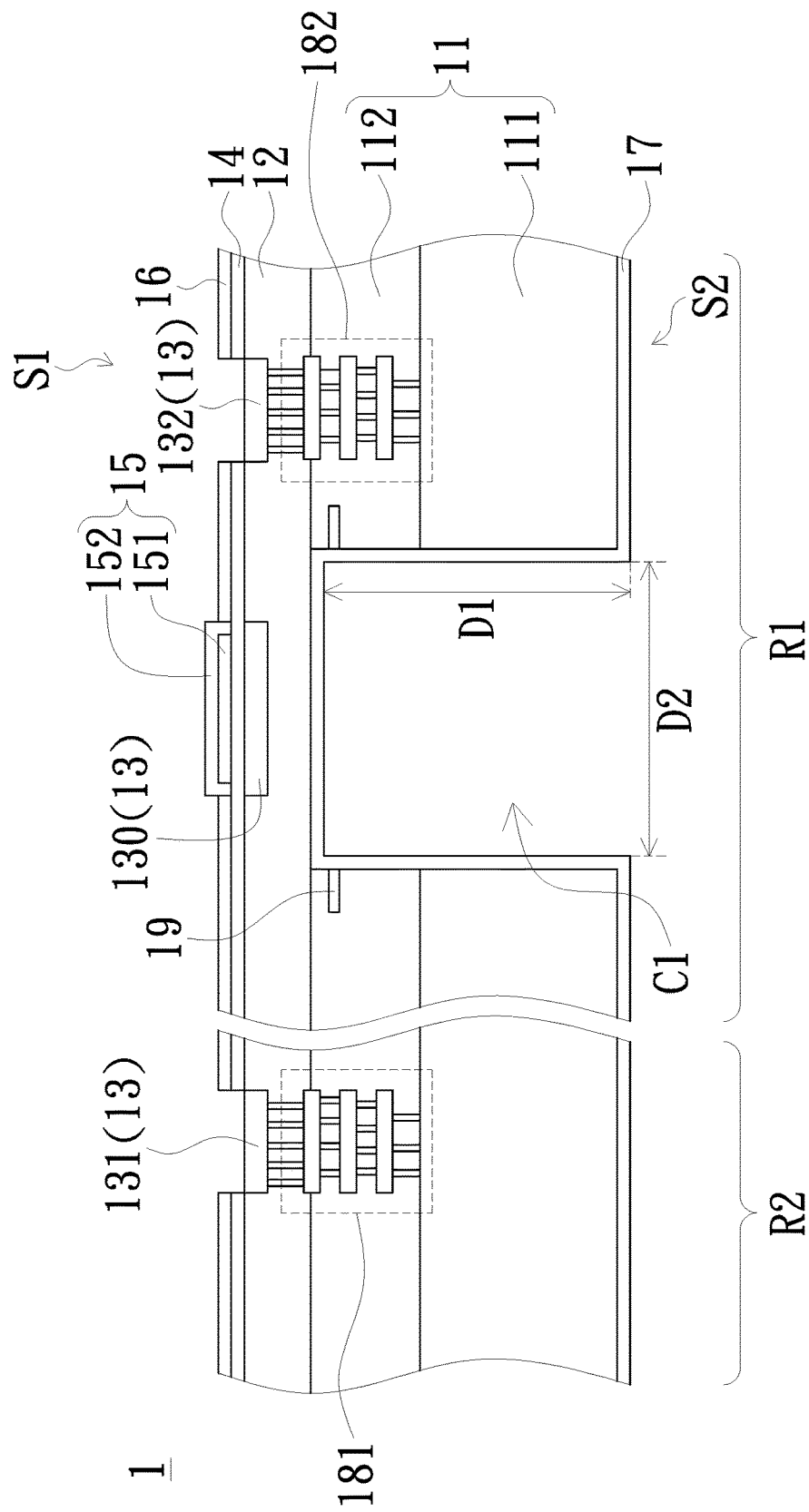

STRUCTURE OF GAS SENSOR

FIELD OF THE INVENTION

The present invention relates to a structure of a gas sensor, especially a gas sensor with better moisture proof.

BACKGROUND OF THE INVENTION

There are various existing gas sensors formed with a sensitive film, a physical value of which is changed by adsorption, desorption or the like of a gas, on a substrate. The film is capable of calculating a concentration of the gas by measuring the change in the physical value of the sensitive film. Favorable characteristics of a gas sensor include high sensitivity, excellent selectivity, high response speed, reliability, ease of fabrication, small-size, and low power consumption.

Sensitivity or selectivity of such a gas sensor is significantly dependent on the temperature of the sensitive film, and therefore a heater is provided in the vicinity of the film and the temperature of the film is controlled to a specific temperature (300° C. to 500° C.) by using, for example, a control circuit. However, in order for gas permeability, it is difficult to avoid oxidation of the heater, and it results in measurement error.

Thus, the present invention provides a gas sensor structure and manufacturing method thereof to solve the above issues.

SUMMARY OF THE INVENTION

The present invention provides a structure of a gas sensor, comprising: a support, having a front side, a back side opposite to the front side, a cell region, and a peripheral region circling the cell region; a cavity, formed on the back side of the support in the cell region; a heater, disposed on the front side of the support covering the cavity; a sensing element, disposed on the heater; and a sealing layer, formed on the back side of the support covering inside the cavity.

In one embodiment of the present invention, wherein the support comprises a silicon layer at the back side and an oxide layer adjacent to the silicon layer at the front side.

In one embodiment of the present invention, wherein the silicon layer is a crystalline silicon layer having a thickness in a range of 290-450 micrometers.

In one embodiment of the present invention, wherein the thickness of the silicon layer is in a range of 350-400 micrometers.

In one embodiment of the present invention, the gas sensor further comprising: an interconnect structure, formed in the oxide layer in the peripheral region.

In one embodiment of the present invention, wherein the oxide layer has a thickness in a range of 6-50 micrometers.

In one embodiment of the present invention, wherein the sealing layer conformally covers on the back side of the support and in the cavity.

In one embodiment of the present invention, wherein the sealing layer has a thickness in a range of 500-10000 angstroms.

In one embodiment of the present invention, wherein the sealing layer has a thickness in a range of 1000-6000 angstroms.

In one embodiment of the present invention, wherein a material of the sealing layer is selected from silicon nitride and polyamide.

In one embodiment of the present invention, wherein the heater is embedded in a dielectric layer and the dielectric layer is disposed directly on the support.

In one embodiment of the present invention, wherein a depth of the cavity is in a range of 300-500 micrometers.

In one embodiment of the present invention, wherein a diameter of the cavity is in a range of 250-700 micrometers.

Accordingly, the present invention provides a structure of a gas sensor with improved moisture proof, and in addition, the sealing layer of the present invention can also provide stress in order to prevent wafer bending. Therefore, oxidation of the heater can be highly prevent and also product yield can be improved.

BRIEF DESCRIPTION OF THE DRAWINGS

The present invention will become more readily apparent to those ordinarily skilled in the art after reviewing the following detailed description and accompanying drawings, in which:

FIG. 1 is a cross-sectional view of the gas sensor according to an embodiment of the present invention.

DETAILED DESCRIPTION OF PREFERRED EMBODIMENTS

The present invention provides a structure of a gas sensor. It is to be noted that the following descriptions of preferred embodiments of this invention are presented herein for purpose of illustration and description only but not intended to be exhaustive or to be limited to the precise form disclosed.

In the following illustration, the element arranged repeatedly is described in word "one", "a" or "an" for simpler explanation. However, one skilled in the art should understand the practical structure and arrangement of each element based on the following illustration and FIGURES provided in the present application.

A gas sensor 1 as shown in FIG. 1 is provided according to an embodiment of the present invention, for the sake of illustration but not meant to be limiting the scope of present invention. The gas sensor 1 comprises: a support 11, having a front side S1, a back side S2 opposite to the front side S1, a cell region R1, and a peripheral region R2 circling the cell region R1; a cavity C1 formed on the back side R1 of the support 11 in the cell region R1; a heater 13 disposed on the front side R1 of the support 11 embedded in a dielectric layer 12 and covering the cavity C1, wherein the dielectric layer 12 is disposed directly on the support 11 and exposes a top surface of the heater 13; a sensing element 15, disposed on the heater 13 and covered by the heater 13; and a sealing layer 17, formed on the back side S2 of the support 11 covering inside the cavity C1. The sensing element 15 comprises a plurality of electrodes 151 (shown as a rectangular object in FIG. 1 for illustration purpose only) and a sensing material 152 covering on all of exposed surface(s) of the electrodes 151. The support 11 comprises a silicon layer 111 at the back side S2 and an oxide layer 112 directly contacting to the silicon layer 111 at the front side S1. The sensing element 15 and the heater 13 can be separated by an insulating layer 14, and a barrier layer 16 is optionally formed covering the front side S1 of the support 11 on the insulating layer 14, wherein the sensing element 15 is partially embedded in the barrier layer 16 and at least a top surface of the sensing element 15 is exposed from the barrier layer 16. Moreover, the heater 13 includes a circuit portion 130 and a plurality of electrodes 131 and 132; an interconnect structure 181 (includes a plurality of interconnect metal layers; and FIG. 1 shows merely three interconnect metal layers for the sake of illustration only but not intending to limit the scope of present invention) may be formed in the oxide layer 112 in the peripheral region R2 to electrically-connect the electrode 131 of the heater 13, and an interconnect structure 182 (includes a plurality of interconnect metal layers; and FIG. 1 shows merely three interconnect metal layers for the sake of illustration only but not intending to limit the scope of present invention) may be formed in the oxide layer 112 in the cell region R1 to electrically-connect the electrode 132 of the heater 13. FIG. 1 shows only partial of a cross-sectional view of the gas sensor 1 that the peripheral region R2 is only a lateral side (connection of the peripheral region R2 and the cell region R1 has an extending direction the same as an extending direction of the support 11) of the cell region R1; however, the peripheral region R2 encircles the cell region R1 from a top view of the gas sensor 1 (not shown).

In the present invention, the silicon layer 111 is a crystalline silicon layer (can be single crystalline or polycrystalline), and the sealing layer 17 conformally covers on the back side S2 of the support S1 and also in the cavity C1. Regarding to materials of other layers/elements, for example, the material of the sealing layer 17 is selected from silicon nitride and polyamide, the barrier layer 16 can be made of nitride, the dielectric layer 12 and the oxide layer 112 can be made of silicon dioxide, the electrodes 151 can be made of platinum, the insulating layer 14 can be made of silicon nitride, and the heater 13 (including the circuit portion 130 and the electrodes 131 and 132) can be made of titanium nitride (TiN) or metal (e.g. tungsten). The above and/or other elements/layers can also be made of materials known in the prior art, and detailed illustration is omitted for purpose of brevity.

Depending on different embodiments and different requirements, a top surface (opposite to the back side S2) of the heater 13 is coplanar with a top surface of the dielectric layer 12. And an etch stop layer 19 is optionally formed inside the oxide layer 112 (the position of the etch stop layer 19 is laterally in-between the upper two interconnect metal layer of the interconnect structure 181 working as an etch stop layer in the step of forming the cavity C1). The etch stop layer 19 is made of amorphous silicon or other appropriate materials having etching selectivity to the oxide layer 112 (and may also to the silicon layer 111). The etch stop layer 19 has a thickness in a range of 0.3-1.0 micrometer; and in an embodiment of the present invention, the etch stop layer 19 has a thickness of 0.5 micrometer.

And for the purpose of performance improvement and reduced product sizes, a thickness of the silicon layer 111 is in a range of 290-450 micrometers, and preferably 350-400 micrometers; a thickness of the oxide layer 112 is in a range of 6-50 micrometers; a thickness of the dielectric layer 12 is in a range of 1-5 micrometers; a thickness of the heater 13 is less than that of the dielectric layer 12, wherein the heater 13 is covered by the dielectric layer 12 from the back side S2 and exposed by the dielectric layer 12 from the front side S1; a thickness of the insulating layer 14 is in a range of 0.2-0.8 micrometers; a thickness of the barrier layer 16 is in a range of 0.2-0.8 micrometers; and a thickness of the sealing layer 17 is in a range of 500-10000 angstroms, and preferably in a range of 1000-6000 angstroms. Moreover, a depth D1 of the cavity C1 is in a range of 300-500 micrometers, and a diameter D2 of the cavity C1 is in a range of 250-700 micrometers.

As shown in FIG. 1 for illustrating the present invention, the cavity C1 can be a through hole penetrating through the support 11, or as in another embodiment of the present invention, the cavity C1 can be a blind hole opened on the back side S2 and stopped in the oxide layer 112. The cavity C1 being a through hole or a blind hole depends on thicknesses of the oxide layer 112 and the dielectric layer 12 (i.e. depending on distance between the cavity C1 and the circuit portion 130 of the heater 13) in different embodiments for different requirements. The cavity C1 is below the heater 13 and also covers the entire circuit portion 130 of the heater 13, and thus the cavity C1 can work as a heat isolation and improve sensor stability. However, only the dielectric layer 12 (and/or the oxide layer 112 in those embodiments having the cavities C1 being as blind holes) cannot prevent moisture from entering, and thus it results in oxidation of the heater 15. Gas sensing errors results from the oxidation of the heater 15 cannot be prevented in a conventional structure of a gas sensor. The sealing layer 17 of the present invention can efficiently prevent moisture in the air from entering through the dielectric layer 12 (and/or the oxide layer 112) to generate oxidation of the heater 13 and thus improve product performance over time. In addition, in the case of the sealing layer 17 being made of nitride, the sealing layer 17 can provide compression/tensile stress to balance stress of if there's a nitride layer on the front side S1 of the support. Therefore, even the silicon layer 111 is thin-down to a range of thickness as provided above for minimize the product size, the support does not bend or warpage, and thus product yield can be improved.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A structure of a gas sensor, comprising:
   a support, having a front side, a back side opposite to the front side, a cell region, and a peripheral region circling the cell region, wherein the support comprises a silicon layer at the back side and an oxide layer adjacent to the silicon layer at the front side;
   a cavity, formed on the back side of the support in the cell region;
   a heater, disposed on the front side of the support covering the cavity;
   a sensing element, disposed on the heater;
   an interconnect structure formed in the oxide layer in the peripheral region, wherein the interconnect structure comprises a plurality of interconnect metal layers; and
   a sealing layer, formed on the back side of the support covering inside the cavity, wherein the sealing layer conformally covers on the back side of the support and in the cavity.

2. The structure of the gas sensor according to claim 1, wherein the silicon layer is a crystalline silicon layer having a thickness in a range of 290-450 micrometers.

3. The structure of the gas sensor according to claim 2, wherein the thickness of the silicon layer is in a range of 350-400 micrometers.

4. The structure of the gas sensor according to claim 1, wherein the oxide layer has a thickness in a range of 6-50 micrometers.

5. The structure of the gas sensor according to claim 1, wherein the sealing layer has a thickness in a range of 500-10000 angstroms.

6. The structure of the gas sensor according to claim 1, wherein the sealing layer has a thickness in a range of 1000-6000 angstroms.

7. The structure of the gas sensor according to claim 1, wherein a material of the sealing layer is selected from silicon nitride and polyamide.

8. The structure of the gas sensor according to claim 1, wherein the heater is embedded in a dielectric layer, and the dielectric layer is disposed directly on the support.

9. The structure of the gas sensor according to claim 1, wherein a depth of the cavity is in a range of 300-500 micrometers.

10. The structure of the gas sensor according to claim 1, wherein a diameter of the cavity is in a range of 250-700 micrometers.

\* \* \* \* \*